(12) United States Patent
Bertacco et al.

(10) Patent No.: US 11,534,760 B2
(45) Date of Patent: Dec. 27, 2022

(54) DEVICE AND METHOD FOR THE QUANTIFICATION OF CELLULAR AND NON-CELLULAR BLOOD COMPONENTS

(71) Applicant: Politecnico di Milano, Milan (IT)

(72) Inventors: Riccardo Bertacco, Milan (IT); Daniela Petti, Milan (IT); Giorgio Ferrari, Milan (IT); Edoardo Albisetti, Milan (IT); Marco Giacometti, Milan (IT)

(73) Assignee: Politecnico Di Milano, Milan (IT)

( * ) Notice: Subject to any disclaimer, the term of this patent is extended or adjusted under 35 U.S.C. 154(b) by 239 days.

(21) Appl. No.: 16/630,702

(22) PCT Filed: Jul. 17, 2018

(86) PCT No.: PCT/IB2018/055278
§ 371 (c)(1),
(2) Date: Jan. 13, 2020

(87) PCT Pub. No.: WO2019/016691
PCT Pub. Date: Jan. 24, 2019

(65) Prior Publication Data
US 2021/0086182 A1    Mar. 25, 2021

(30) Foreign Application Priority Data
Jul. 19, 2017    (IT) .................. 102017000082112

(51) Int. Cl.
*B01L 3/00* (2006.01)
*G01N 27/74* (2006.01)
*G01R 33/12* (2006.01)

(52) U.S. Cl.
CPC ... *B01L 3/502761* (2013.01); *B01L 3/502715* (2013.01); *G01N 27/745* (2013.01);
(Continued)

(58) Field of Classification Search
CPC ......... B01L 3/502761; B01L 3/502715; B01L 2300/0645; B01L 2400/043; G01N 27/745; G01R 33/1276
See application file for complete search history.

(56) References Cited

PUBLICATIONS

Chung Y K et al: "An electrical biosensor for the detection of circulating tumor cells", Boosensors and Bioelectronics, vol. 26, Jan. 15, 2011, pp. 2520-2526 (Year: 2011).*
(Continued)

*Primary Examiner* — Robert J Eom
(74) *Attorney, Agent, or Firm* — Mark Malek; Widerman Malek, PL (57) ABSTRACT

A device for the quantification of cellular and non-cellular components in a blood sample including detection electrodes including a first electrode connected with a first input to receive a first signal in input and a second electrode, reference electrodes including a first electrode connected with a second input configured to receive a second signal in input of opposite polarity to the first input signal and a second electrode connected to the second electrode of said detection electrodes, in a common point wherefrom an output signal is picked up, a ferromagnetic concentrator that cooperates with an external magnetic field external to effectuate concentration of said components on said detection electrodes, a substrate configured to house said detection electrodes, reference electrodes, and concentrator; a support configured to collect a blood sample, and a spacer element to confine in the substrate plane the blood sample and to distance said substrate from said support.

5 Claims, 6 Drawing Sheets

(52) U.S. Cl.
CPC .. *G01R 33/1276* (2013.01); *B01L 2300/0645* (2013.01); *B01L 2400/043* (2013.01)

(56) References Cited

PUBLICATIONS

Malic, L., et al. "Polymer-based microfluidic chip for rapid and efficient immunomagnetic capture and release of Listeria monocytogenes." Lab on a Chip 15.20 (2015): 3994-4007. (Year: 2015).*

Li, Chen, et al. "Research progress on microfluidic chip of cell separation based on dielectrophoresis." Chinese Journal of Analytical Chemistry 43.2 (2015): 300-309. (Year: 2015).*

Yang, Mo, and Xin Zhang. "Electrical assisted patterning of cardiac myocytes with controlled macroscopic anisotropy using a microfluidic dielectrophoresis chip." Sensors and Actuators A: Physical 135.1 (2007): 73-79. (Year: 2007).*

* cited by examiner

DEVICE AND METHOD FOR THE QUANTIFICATION OF CELLULAR AND NON-CELLULAR BLOOD COMPONENTS

RELATED APPLICATIONS

This application is related to international patent application PCT/IB2018/055278 filed on Jul. 17, 2018 and titled Device and Method for the Quantification of Cellular and Non-Cellular Blood Components, the entire content(s) of which is/are incorporated herein by reference.

TECHNICAL FIELD

The present invention relates to a device and relative method for the quantification of corpusculated and non-corpusculated components present in a solution containing a blood sample, by means of the concentration and magnetophoretic separation of the components of interest from the rest of the sample and the impedentiometric detection of the quantity of these components.

DESCRIPTION OF THE RELATED ART

For the purposes of the present description "corpusculated components" refer to the cell components of the blood such as red blood cells, white blood cells and platelets.

"Non-corpusculated components" refer instead to those non-cell components, in any case with a volume smaller than or comparable to that of the cells, yet greater than that of the single molecules. These non-corpusculated components can be, for example, crystals of some substances which develop in particular pathological conditions, such as for example the crystals of haemozoin produced by the plasmodium of malaria.

More particularly, the present invention relates to a device and relative method which allows and provides for the isolating and concentrating spatially of one or more corpusculated haemocomponents, as well as one or more substances present in the plasma, exploiting the differences between the magnetic properties of said haemocomponents and/or said substances and the magnetic properties of the other haemocomponents or substances not of interest.

Once separation and concentration have taken place, the device and the relative method of the present invention provide, therefore, for the quantification, of these corpusculated haemocomponents and/or of these substances present in the plasma to take place by means of the measurement of the variation in impedance between two or more electrodes placed in proximity of the zones of concentration.

The field of application of the present invention relates therefore to the diagnosis of all those pathologies that cause an alteration of the magnetic properties of one or more types of blood corpuscles and/or give rise to the formation of substances with different magnetic properties from plasma, said substances being absent or in a different concentration in physiological conditions.

More particularly, pathologies are known that cause the alteration of the magnetic properties of the erythrocytes, or red blood cells, such as malaria, as well as pathologies which cause the alteration of the magnetic properties of the white blood cells. For example, in the case of malaria, it is known how the plasmodium, during the malaria pathogenesis, produces a particular substance mentioned above, which takes the name of haemozoin and is a paramagnetic substance. More particularly, the haemozoin is produced in the form of crystals which are accumulated in the infected erythrocytes, making them paramagnetic. Moreover, in the non-early phases of malaria, the membrane of the infected red blood cells breaks, giving rise to the release of the crystals of haemozoin in the plasma, which is, instead, diamagnetic.

Pathologies are also known in which it is not the magnetic properties of corpuscles of the blood that vary but instead their density. An example of this type comes from sickle cell anaemia, where, while the diamagnetism of the red blood cells remains unchanged, their density changes. In this case, by adding a strongly paramagnetic substance to the plasma, such as for example gadolinium, it can be thought to exploit the magnetic difference between the red blood cells and the gadolinium solution added to the plasma together with the difference in density between the sick red blood cells and healthy red blood cells in order to obtain the separation and, therefore, perform the count of the pathological erythrocytes.

At the state of the art, techniques are known of separation of corpusculated components of the blood, based on the different magnetic behaviour assumed by these components in physiological and pathological conditions.

More particularly, in the patent application U.S. Pat. No. 5,985,153A a device is described for the separation of cells or other magneto-sensitive biological entities comprising: a substrate, a generator of an external magnetic field and a microfluidic system for the loading and unloading of the blood.

In document US0127222A a generic system is instead described for the immobilisation of cells previously marked with magnetic particles, in such a way that they can be attracted by ferromagnetic structures formed on a chip and placed in an external magnetic field.

In the application WO2010091874 a particular ferromagnetic structure is described, composed of magnetic conduits, capable of attracting magnetic particles in particular points in which magnetic domain walls are located. In all the prior art documents mentioned above, as well as in a part of the scientific literature listed in the bibliography [S. Bhakdi et al., *Optimized high gradient magnetic separation for isolation of Plasmodium-infected red blood cells, Malaria Journal* 2010, 9:38]; [J. Nam et al., *Magnetic Separation of Malaria-Infected Red Blood Cells in Various Developmental Stages, Anal. Chem.*, 85, 7316-7323 (2013)]; [Ki-Ho Han and A. Bruno Frazier, *Paramagnetic capture mode magnetophoretic microseparator for high efficiency blood cell separations, Lab Chip*, 6, 265-273 (2006)], only the magnetophoretic separation of the components of interest from the rest of the blood sample is described, and no mention is made of the detection of the number of these components.

In the patent application US20120003687A and in the scientific publications [E. Du, et al., *Electric Impedance Microflow Cytometry for Characterization of Cell Disease States, Lab Chip.* 2013 Oct. 7; 13(19): 3903-3909] e [M. Ibrahim, J. Claude, D. Kourtiche and M. Nadi, *Geometric parameters optimization of planar interdigitated electrodes for bioimpedance spectroscopy, J Electr Bioimp*, vol. 4, pp. 13-22, 2013] techniques of impedentiometric quantification of corpusculated components are described.

These techniques have not however ever been used in association with magnetophoretic separation and concentration. Impedentiometric detection requires that the volumetric fraction of the corpuscles in proximity of the electrodes is sufficiently high, in order to obtain a signal-to-noise ratio in the output signal which is sufficient in order to guarantee a correct quantification of the separated components.

This concentration is usually obtained with microfluidics techniques which considerably increase the degree of complexity of the system and make it poorly suited to a use by a non-specialised user, for example the actual patient.

The device proposed intends to overcome these difficulties by replacing the microfluidics part with a system of magnetic separation and concentration of the components of interest on zones of the substrate in which the detection electrodes are located. In order to perform the measurement the non-specialised user has to dispense on the support a drop of newly sampled blood and then place it in contact with the substrate on which the concentrator elements and the electrodes are housed, in turn placed face downwards within an external magnetic field.

For a volume of the drop of blood sampled of the order of around ten microlitres and supposing that the capture of the components of interest takes place at most at a distance from the concentrators comprised between 20 and 200 micrometres, the dimensions of the active area for the capture on the substrate must be of the order of a few $cm^2$ and, in particular, comprised between 0.5 and 5 $cm_2$. The support must also have approximately the same dimensions.

On these values of active area a high concentration of components of interest is necessary in order to ensure an adequate signal-to-noise ratio. As will be explained in greater detail here below, this concentration can be quantified by means of a so-called concentration factor Fe which comes from the ratio between the active area of the substrate within which the drop containing the components which are to be quantified is confined and the area defined by the detection electrodes. In order to have an adequate signal-to-noise ratio in the output signal the concentration factor Fe must preferably be at least around 100.

The object of the present invention is therefore that of providing a device and relative method which are able to quantify the haematic components of interest starting from a quantity of blood such as that which can be extracted by means of pricking with a needle the finger of a patient (5-10 microL) and produce a signal in output with a signal-to-noise ratio such as to allow the detection of corpusculated and non-corpusculated components of the blood with lower limit of concentration up to 10 components per microlitre.

This object is achieved by the present invention with a measurement of the impedentiometric type performed by means of appropriate detection electrodes. The device of the present invention comprises, in fact:

- at least one pair of detection electrodes, said at least one pair of detection electrodes comprising at least one first electrode connected with a first input apt to receive a first signal in input (V+) and a second electrode;
- at least one pair of reference electrodes; said at least one pair of reference electrodes comprising a first electrode connected with a second input configured to receive a second signal in input (V+) of opposite polarity to the first input signal (V+) and a second electrode connected to the second electrode of said at least one pair of detection electrodes, in a common point wherefrom an output signal (Out) is picked up;
- at least one concentrator of ferromagnetic material, configured to co-operate with a magnetic field external to the device, in such a way as to cause the concentration of said components on said at least one pair of detection electrodes;
- a substrate configured for the housing of: said at least one pair of detection electrodes; said at least one pair of reference electrodes and said at least one concentrator;
- a support configured to receive a sample of blood or of solution containing blood; and
- at least one spacer element, configured to confine in the plane of the substrate the blood sample and to distance said substrate from said support.

Said at least one concentrator can be a cylinder or a parallelepiped or an element of another shape placed on the substrate, placed at the detection electrodes and is constituted by ferromagnetic material. The concentrator, attracting towards itself the components to be quantified, ensures that the latter are not distributed everywhere in the area covered by the substrate but concentrate, instead, in proximity of said concentrator, and therefore in proximity of the detection electrodes.

In this way, dimensioning appropriately both the concentrator and the detection electrodes, the concentration factor can increase up to the value necessary for obtaining an adequate signal-to-noise ratio.

The device described above co-operates with means for the generation of a static magnetic field, with which it forms an apparatus. These means for the generation of said field are permanent magnets configured so as to generate a magnetic field, optionally, characterised also by a macroscopic gradient.

Said field is able to attract uniformly towards the substrate the components sought, when they are at a great distance from the concentrators, and of magnetising the aforementioned concentrators to create therefore an intense local magnetic field gradient, which completes the separation of the components to be quantified from the rest of the solution and produces their accumulation on the concentrators.

This separation takes place thanks to the competition between the gravitational force which aims towards the ground and the magnetic attraction force in the direction opposite to that of the gravitational force. The detection electrodes are placed in proximity of said concentrator elements, while the reference ones are placed in areas without said concentrators.

In this way the separated components accumulate selectively on the detection electrodes but not on the reference ones, causing a specific variation of the impedance between the detection electrodes with respect to the spurious one possibly recorded between the reference electrodes. The output signal of the impedentiometric quantification system is therefore proportional to the difference between the impedance variation recorded between the detection electrodes and the one between the reference electrodes. The number of components of interest of this output signal can then be estimated through comparison with an appropriate calibration curve, performed by means of a processor.

As mentioned above, the device and relative method of the present invention can be applied to the diagnosis of any pathology which is the cause of a variation of the magnetic properties of one more haematic components, as well as to the diagnosis of pathologies which cause a variation in the density of one or more components, in this case providing for the addition in the sample of blood to be analysed of a solution of different magnetic properties with respect to the plasma.

Among the various pathologies for the diagnosis of which it is possible to use the device of the present invention, malaria is however of particular interest, in that the diagnostic devices for this type of pathology, today present on the market, have some limitations which make them not always easy to use in particularly disadvantaged contexts, such as the typical ones of endemic zones, often located in developing countries. The most sensitive method currently available for the diagnosis of malaria is based in fact on gene recognition of the various strains of plasmodium by means of PCR (polymerase chain reaction).

This type of method is particularly complex and delicate and, therefore, difficult to apply in contexts that are not technologically advanced. Moreover PCR is not a pan-plasmodium method but is targeted at specific strains and subject, therefore, to the problems arising from the continuous mutations of the plasmodium.

The method, instead, of the "thin smear and/or thick drop" which consists in counting under the optical microscope the red blood cells infected by the plasmodium in a drop of blood, while not requiring complex instrumentation, needs highly expert staff, entails a certain variability in the interpretation of the results and long analysis times.

The rapid tests (RDT) based on the antibody-antigen interaction are, instead, characterised by such low sensitivity as to prevent use thereof for early diagnosis. Moreover, due to the latent presence of the antigen in the body of patients in an endemic zone, the methods based on the antibody-antigen interaction give rise to a high number of false positives.

A second object of the present invention is therefore that of providing a device and relative method which also allow the early diagnosis of malaria, is pan-plasmodium, has adequate sensitivity and is of such simplicity and economical nature as to be able to be used also in those zones where the economic means available do not allow the use of complex instruments and specialist personnel.

This object is achieved by the device and method of the present invention, in that the latter is able to perform the magnetic separation and the quantification both of the infected erythrocytes and the magnetic separation and direct detection of the free haemozoin crystals in the plasma.

The quantification of the infected erythrocytes allows a direct valuation of the parasitemia to be obtained, which is normally quantified by calculating the ratio between infected erythrocytes and healthy erythrocytes, optionally also in the early phase of the disease, before the completion of the first cycle of reproduction of the plasmodium (48-72 hours).

The direct detection of the crystals of haemozoin is, instead, particularly useful, in the non-initial phases of the disease, such as for example concurrent with the first fever attack, since, in these phases, the erythrocytes have already undergone the breakage of the membrane, and the only thing which can effectively be quantified in circulation is the free haemozoin.

These and further objects of the present invention will be made clearer by the reading of the following detailed description of some preferred embodiments of the present invention, to be understood by way of a non-limiting example of the more general concepts claimed, and from the examples relating to experimental tests performed on the present invention.

BRIEF DESCRIPTION OF THE DRAWINGS

The following description refers to the accompanying drawings in which.

DETAILED DESCRIPTION

Referring to FIGS. 1, 3a, 3b and 3c and 5, the device (1) of the present invention comprises:

- a plurality of detection electrodes (4, 4', 5, 5', 6, 6', 34, 34'),
- a pair of reference electrodes (7, 7', 8, 8', 9, 9', 37, 37') for each pair of
- detection electrodes (4, 4', 5, 5' 6, 6', 34, 34');
- a concentrator (10, 10', 10", 14, 14', 14") for each pair of detection electrodes (4, 4', 5, 5', 6, 6'), said concentrator (10, 10', 10") being configured to attract magnetically the components (3, 3', 3") to be quantified and concentrate said components on the detection electrodes (4, 4', 5, 5'*t* 6, 6'*t* 34, 34');
- a substrate (11) configured for the housing of the detection electrodes (4, 4', 5, 5', 6, 6', 34, 34'), of the reference electrodes (7, 7', 8, 8', 9, 9', 37, 37') and of the concentrators (10, 10', 10", 14, 14', 14");
- a support (12) configured to receive a sample of blood or of solution containing blood; and
- at least one spacer element (13, 13') configured to confine the sample to be analysed and to distance said substrate (11) from said support (12).

Said at least one spacer element (13, 13') can be ring shaped.

Figure 1:
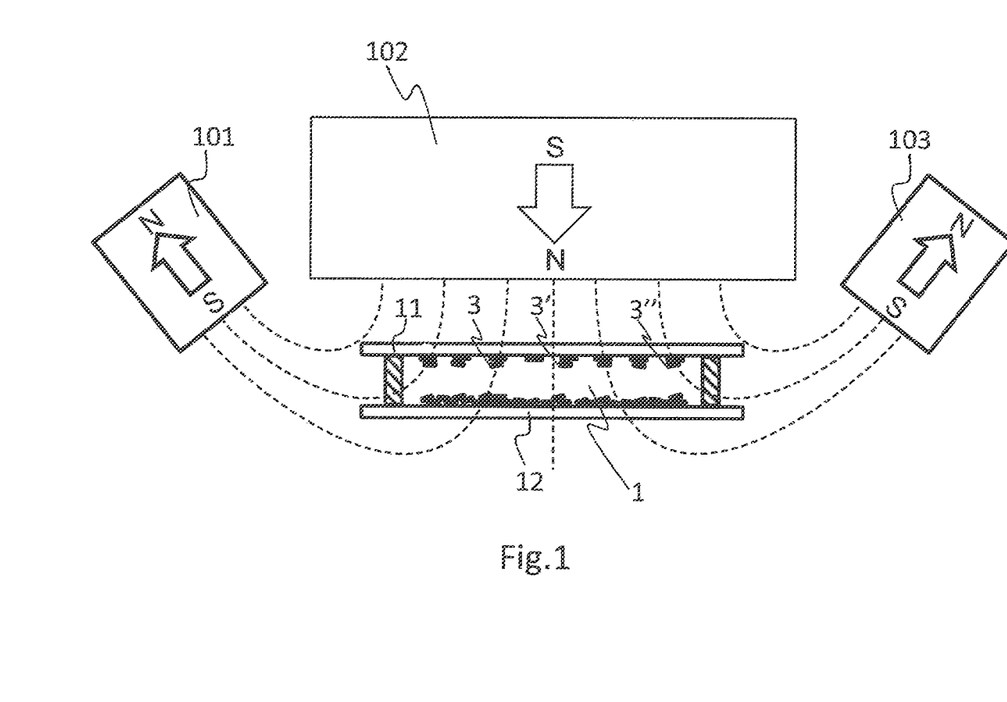
FIG. 1 is an overall diagram of an apparatus comprising a device according to the present invention apt to be used for the diagnosis of malaria.

The device (1) of the present invention can be inserted inside an apparatus (100) comprising also:

- an electronic unit for the generation of the input signals, the readings of the signals generated by the electrodes (7', 8', 9', 4', 5', 6', 34', 37') and their processing;
- a housing configured for the positioning of said device (1);
- a plurality of connectors for the connection between said device (1) and
- said electronic unit; and
- means for the generation of a static magnetic field (101, 102, 103), said means (101, 102, 103) being configured to generate a magnetic field able to cause the separation of the components (3, 3', 3") to be quantified from the rest of the solution.

In the particular case of malaria, said means (101, 102, 103) for the generation of a static magnetic field are able to generate a field which, preferably, has an intensity of at least $10^4$ A/m and a macroscopic gradient of at least $10^8$ A/m$^2$ aimed towards the substrate or exiting therefrom, respectively in the case of paramagnetic or diamagnetic components with respect to the liquid medium in which they are dispersed.

Said means comprise a plurality of permanent magnets (101, 102, 103) positioned so that the field generated by said magnets (101, 102, 103) overcomes the resultant of the weight force and of that of Archimedes acting on the components of interest at a great distance from the substrate, preventing said components from precipitating on the surface of the support.

Moreover the field generated by said magnets must be able to magnetise effectively the concentrator elements so that they produce an intense gradient of local magnetic field able to attract selectively and concentrate said components (3, 3', 3") only on the areas of the substrate (11), occupied by the detection electrodes (4, 4', 5, 5', 6, 6'), said components (3, 3', 3") being paramagnetic.

It is obvious that in the cases wherein the components to be quantified are diamagnetic, said means for the generation of a static magnetic field comprise a plurality of permanent magnets positioned so that the gradient of the field generated by said magnets is exiting from the substrate, such as to overcome the weight force at a great distance. Similarly, the local field gradient produced by the magnetic concentrators must be exiting from the zones with the detection electrodes and ensure that said components accumulate at said detection electrodes, said components being diamagnetic.

Figure 2:
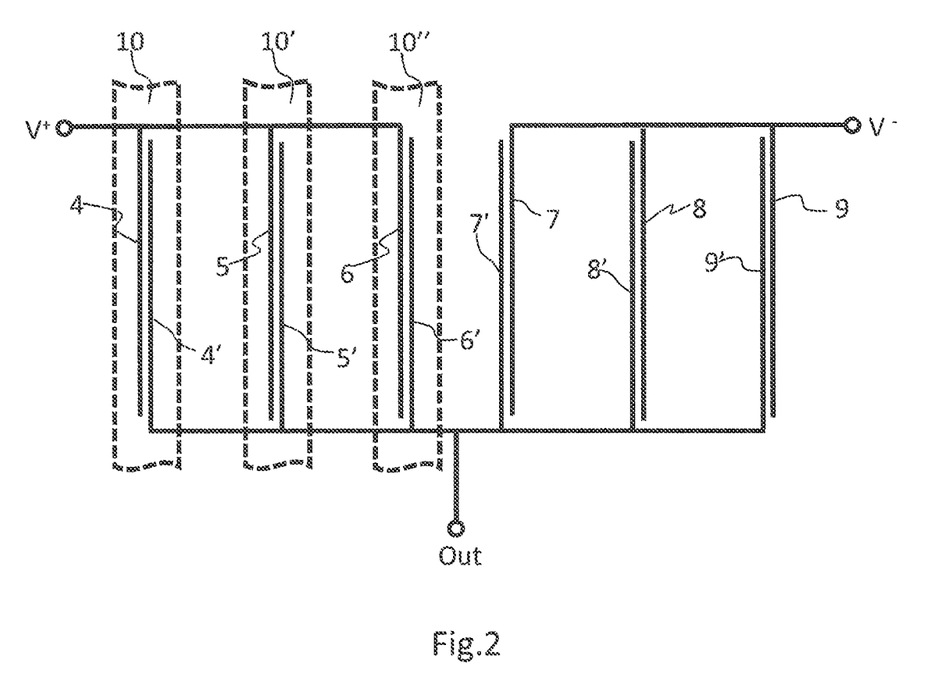
FIG. 2 is an example diagram of the positioning of the detection and reference electrodes with respect to the concentrators, in a first embodiment of the present invention.

Referring to FIG. 2, in a first embodiment of the present invention each pair of detection electrodes (4, 4', 5, 5', 6, 6'), comprises a first electrode (4, 5, 6) apt to receive a first signal in input (V+) and a second electrode (4', 5', 6'). Each pair of reference electrodes (7, 7', 8, 8', 9, 9') comprises a first electrode (7, 8, 9) apt to receive a second signal in input (V−) of opposite polarity to the first input signal (V+) and a second electrode (7', 8', 9') connected to the second electrode (4', 5', 6') of each pair of detection electrodes (4, 4', 5, 5', 6, 6'), in a common point from which the output signal (Out) is picked up.

Figure 3A:
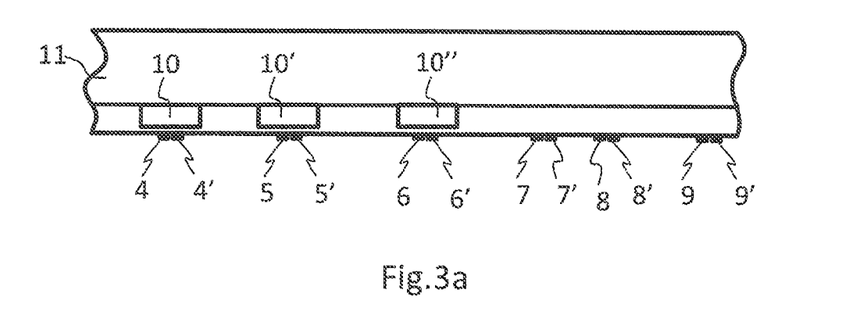
FIG. 3a shows a section of a first embodiment of the device of the present invention, said section being along a plane perpendicular to the greater dimension of said at least one concentrator.
Figure 3B:
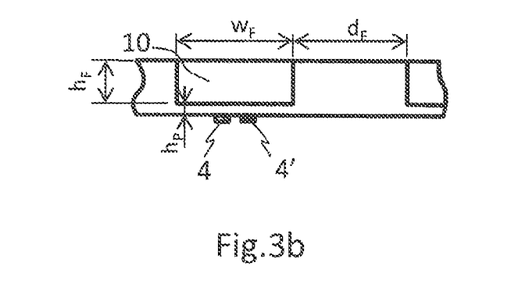
FIG. 3b shows a detail of the section shown in FIG. 3a, relating to said at least one concentrator.
Figure 3C:
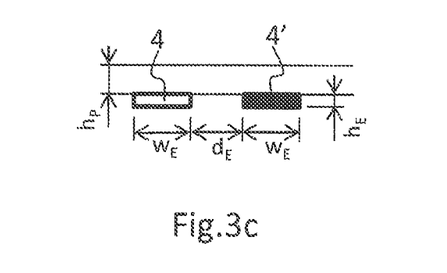
FIG. 3c shows a detail of the section shown in FIG. 3a, relating to said at least one pair of detection electrodes.

Referring to FIGS. 3a, 3b, 3c, in a first embodiment of the present invention, apt for the diagnosis of malaria, the concentrators (10, 10', 10") are made of ferromagnetic material, such as Ni, Fe, Co, NiFe, CoFe, etc., and have the shape of a parallelepiped with the greater dimension which extends perpendicularly to the plane shown in FIG. 3a. In order to guarantee a sufficient concentration factor for obtaining an adequate signal-to-noise ratio, the dimensions of the concentrators (10, 10', 10") and of the detection electrodes (4, 4', 5, 5', 6, 6') must be, preferably, comprised within the ranges listed in Table 1.

TABLE 1

$h_F$ is the smaller dimension of the base of a concentrator, $w_F$ is the larger dimension of the base of a concentrator and $d_F$ is the distance between one concentrator and the adjacent concentrator. $h_E$ is the smaller dimension of the base of a detection electrode, $w_E$ the larger dimension of the base of a detection electrode and $d_E$ the distance between two adjacent electrodes at the same concentrator.

| Component | $h_F$ (µm) | $w_F$ (µm) | $d_F$ (µm) | $h_E$ (µm) | $w_E$ (µm) | $d_E$ (µm) |
|---|---|---|---|---|---|---|
| i-RBC | 10-30 | 30-60 | 30-60 | 10-300 | 2-6 | 2-6 |
| HC | 5-10 | 15-30 | 15-30 | 10-300 | 1-3 | 1-5 |

In the first row of Table 1, the ranges are shown of the dimensions of the concentrators and of the detection electrodes necessary for a correct detection of the erythrocytes infected (i-RBC) by the plasmodium of the malaria. While in the second row of Table 1 the ranges are shown of the dimensions of the concentrators and of the detection electrodes necessary for a correct detection of the free crystals of haemozoin (HC).

Figure 4:
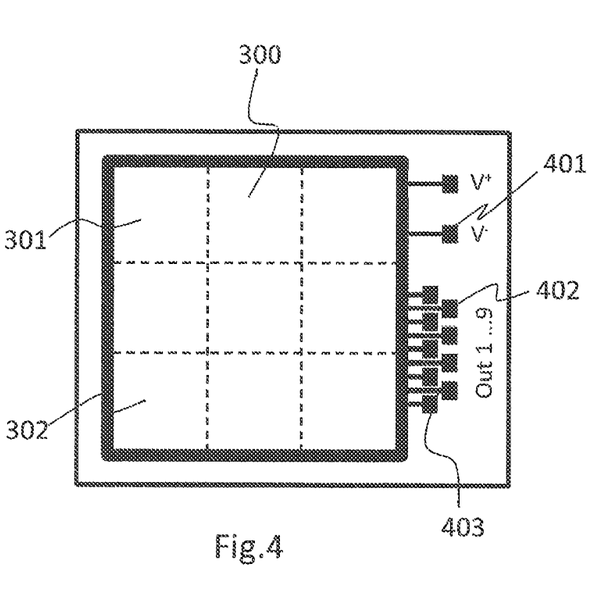
FIG. 4 is a view from above of a first embodiment of the device of the present invention.

Referring to FIG. 4, the substrate (11) and, therefore the actual device (1) of the present invention, the structure of the detection electrodes (4, 4', 5, 5', 6, 6') and of the reference electrodes (7, 7', 8, 8', 9, 9') shown in FIGS. 3a, 3b and 3c, can be replicated in nine square zones (300, 301, 302) into which the substrate (11) is divided. The division of the active area into several regions with independent readings allows an increase in the ratio between the variation in impedance produced by a single component attracted on the detection electrodes and the overall impedance between the electrodes, improving the signal-to-noise ratio in the case of low concentrations of components to be detected. Since for each zone an output contact is necessary towards the amplifier from which to emit the output signal (Out), while all the output signals (V+) and (V−) for detection electrodes and reference electrodes need only two contacts, the total number of contacts to be formed on the chip is equal to 9+2=11. This number is compatible with the positioning of 11 terminals (401, 402, 403) of dimension equal to 400×400 µm on one side of the substrate (11).

Figure 5:
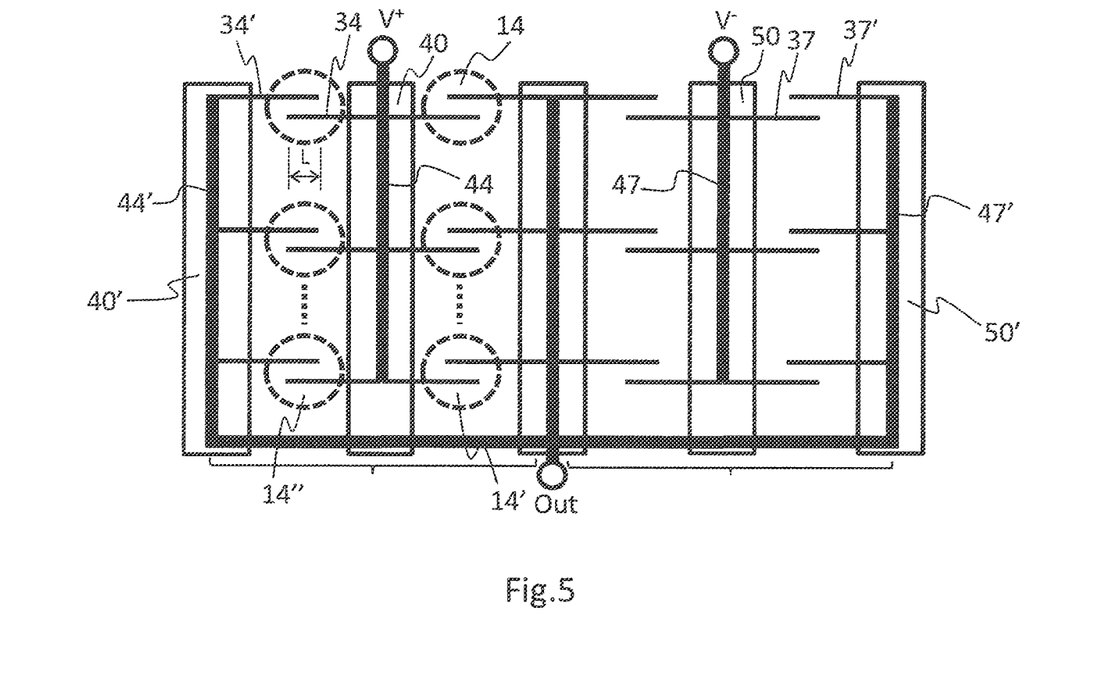
FIG. 5 is a view from above of a detail of a second embodiment of the present invention.

Referring to FIG. 5, a second embodiment of the device of the present invention provides for the use of a matrix of ferromagnetic concentrators of cylindrical shape (14, 14', 14") evenly distributed on the substrate (11). FIG. 5 shows, in particular, six pairs of detection electrodes (34, 34') and six pairs of reference electrodes (37, 37'). The first electrode (34) of each pair of detection electrodes (34, 34') is connected to a first input configured for the reception of the first input signal (V+) by means of a first connection path (44). The first electrode (37) of each pair of reference electrodes (37, 37') is connected to a second input configured for the reception of the second input signal (V−) by means of a second connection path (47). Similarly, the second electrode (34') of each pair of detection electrodes (34, 34') is connected to the node wherefrom the output signal (Out) is emitted by means of a third connection path (44') and the second electrode (37') of each pair of reference electrodes (37, 37') is connected to the node wherefrom said output signal (Out) is emitted by means of a fourth connection path (47'). Above the first connection path (44), the second connection path (47), the third connection path (44') and the fourth connection path (47') an insulating layer (40, 40', 50, 50') is placed for each path, said insulating layer (40, 40', 50, 50') having dielectric constant and thickness such as to make the impedance between said connection paths (44, 44', 47, 37') negligible. The configuration of the concentrators provided by the second embodiment allows a concentration factor to be obtained which is even higher compared to that which can be obtained with respect to the first embodiment. To this end the dimensions of the concentrators (14, 14', 14") and of the detection electrodes (34, 34', 35, 35') must be, preferably, comprised within the ranges listed in Table 2.

TABLE 2

$h_F$ is the height of a concentrator, $w_F$ is the diameter of the base of a concentrator and $d_F$ is the distance between one concentrator and the adjacent concentrator. $h_E$ is the smaller dimension of the base of a detection electrode, $w_F$ is the larger dimension of the base of a detection electrode and $d_E$ the distance between the first detection electrode finger and the second finger of said detection electrode.

| Component | $h_F$ (µm) | $w_F$ (µm) | $d_F$ (µm) | $h_E$ (nm) | $w_E$ (µm) | $d_E$ (µm) |
|---|---|---|---|---|---|---|
| i-RBC and HC | 10-30 | 10-30 | 50-150 | 10-300 | 1-3 | 1-5 |

Table 2 shows the ranges of the dimensions of the concentrators and of the detection electrodes necessary for a correct detection both of the erythrocytes infected (i-RBC) by the plasmodium of the malaria and of the free crystals of haemozoin (HC). With these dimensions, supposing a length L of the electrodes equal to 6 μm, a concentration factor is obtained $$F_C = \frac{(d_F + w_F)^2}{L(2w_E + d_E)}$$

equal to approximately 400.

Example

The example described here below relates to the calculation of the percentage variation of impedance between the detection electrodes and the reference electrodes in a second embodiment of the present device and with reference to the detection of i-RBC. In the particular case a substrate (11) of area equal to 1 cm$_2$ was considered.

The substrate (11) (of dimension 1 cm$^2$) was divided into nine square zones (as in FIG. 4), each one provided with a matrix of 550 concentrators. At the centre of each concentrator a pair of detection electrodes is placed with length L equal to 6 μm, width WE equal to 2 μm and distance between the electrodes $d_E$ of 2 μm. The containment ring with a plurality of spacer elements (13, 13') is such as to impose a distance between the substrates 11 and 12 of 50 μm and the concentrators (10, 10', 10')' allow the capture of all the infected erythrocytes which are found in the volume defined by substrate, support and containment ring. By measuring the impedance at a frequency of the order of 1-20 MHz it is possible to obtain the electrical resistance R of the material between the electrodes, given mainly by the solution and by the possible presence of infected erythrocytes i-RBC captured by the magnetic concentrators.

Figure 6:
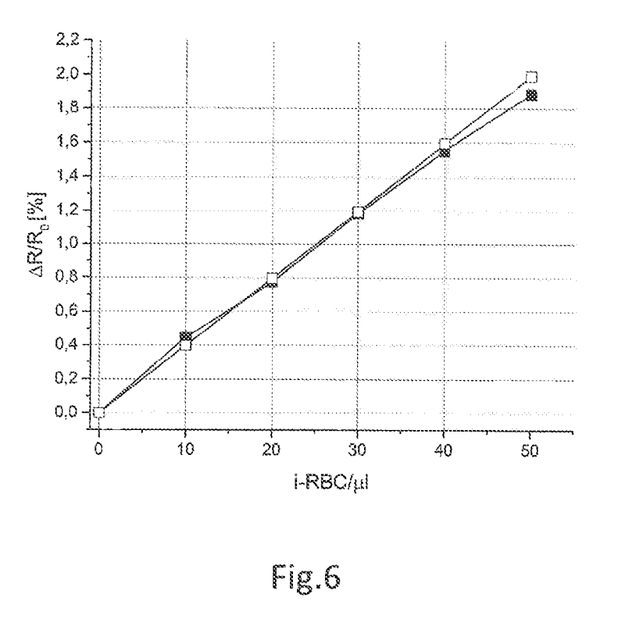
FIG. 6 shows the trend of the percentage resistance variation between the detection electrodes and the reference electrodes as a function of the level of parasitemia generated by the capture of erythrocytes infected by the plasmodium of the malaria, in a second embodiment of the present invention.

FIG. 6 shows the percentage resistance variation $\Delta R/R_0$, as a function of the infected erythrocytes i-RBC captured on the surface of the detection electrodes, obtained by means of finite element simulation (FEM) (full squares) and by means of the following formula (empty squares):

$$\frac{\Delta R}{R_0} = \frac{3}{2} \cdot \frac{V_p}{N \cdot (w_E + d_E) \cdot L \cdot H}$$

where Vp represents the total volume occupied by the i-RBC captured on the surface of the electrodes, while N, H are, respectively, the number of pairs of detection electrodes which share a same output, and the height up to which a pair of detection electrodes is sensitive to the presence of the components of interest, equal to approximately 1-2 times the distance between the electrodes $d_E$. The volume $V_p$ is equal to the volume of a single i-RBC multiplied by the number of erythrocytes captured. The latter is equal to the concentration of infected erythrocytes multiplied by the volume of capture of the concentrators, 1 cm$^2 \cdot d_{capture}$=5 μl.

$\Delta R/R_0$ is in fact proportional to the fraction of the effective volume, to which the impedentiometric measurement is sensitive, occupied by the components of interest. It should be noted in the case of parasitemia equal to 10 parasites/μL (on average 5.5 parasites for each of the nine zones of our geometry), the expected resistance variation, $\Delta R/R_0$, is found to be equal to about 0.4%, corresponding to a resolution required of the reading electronics, in the resistance measurement, equal to approximately 1000 ppm).

Should the system for magnetic concentration (i.e. the whole constituted by external magnets and concentrators) be able to capture the infected erythrocytes at a distance ten times greater, $d_{capture}$=500 μm, and the distance between the substrates 11 and 12 increase correspondingly by a factor 10, it would be possible to arrive at a $\Delta R/R_0$ ten times greater with respect to the previous case, at the same concentration of parasites and active area of the substrate but increasing by a factor 10 the volume of the drop of blood. Or, again with $d_{capture}$=500 μm and height of the container ring with a plurality of spacer elements of 500 μm, the volume of the drop could be kept unchanged at 5 microlitres and a $\Delta R/R_0$ equal to that in FIG. 6 obtained, reducing the active area on the chip.

The invention claimed is:

1. A device for the quantification of cell and non-cell components in a solution containing a blood sample comprising:
   at least one pair of detection electrodes, said at least one pair of detection electrodes comprising at least one first electrode connected with a first input apt to receive a first signal in input (V+) and a second electrode;
   at least one pair of reference electrodes, said at least one pair of reference electrodes comprising a first electrode connected with a second input configured to receive a second signal in input (V+) of opposite polarity to the first input signal (V+) and a second electrode connected to the second electrode of said at least one pair of detection electrodes, in a common point wherefrom an output signal (Out) is picked up;
   said device comprising:
   at least one concentrator in ferromagnetic material and cooperating with a magnetic field external to the device to cause the concentration of said components on said at least one pair of detection electrodes;
   a substrate having a first side and a second side that is opposite of the first side;
   a support configured to receive a sample of blood or of solution containing blood;
   at least one spacer element connected to and extending between said substrate and said support so that the support is spaced apart from the substrate, said at least one spacer element is configured to confine in the plane of the substrate the blood sample and to distance said substrate from said support;
   wherein said at least one pair of detection electrodes are attached to the first side of the substrate;
   wherein said at least one pair of reference electrodes are attached to the second side of the substrate;
   wherein said at least one concentrator is carried by said substrate; and
   wherein said at least one spacer element confines the blood sample in the plane of the substrate so that the blood sample does not contact said substrate, said at least one pair of detection electrodes, and said at least one pair of reference electrodes.

2. The device according to the claim 1, wherein:
   the first electrode of each pair of detection electrodes is connected to the first input by means of a first connection path;
   the first electrode of each pair of reference electrodes is connected to the second input by means of a second connection path;

the second electrode of each pair of detection electrodes is connected to the node wherefrom the output signal (Out) is emitted by means of a third connection path; and the second electrode of each pair of reference electrodes is connected to the node wherefrom said output signal (Out) is emitted by means of a fourth connection path;

above each of said connection paths an insulating layer being placed with such dielectric constant and thickness as to make an impedance between said connection paths negligible.

3. The device according to claim 1, wherein said at least one concentrator is cylindrical in shape, the diameter of the base surface of said concentrators being comprised between 10 and 30 μm, the height of said concentrators being comprised between 10 and 30 μm and the distance between said concentrators being comprised between 50 and 150 μm.

4. The device according to claim 1, wherein the first electrode of said at least one pair of detection electrodes and the second electrode of said at least one pair of detection electrodes are with rectangular section, with base comprised between 10 and 300 nm and height comprised between 1 and 3 μm.

5. The device according to claim 4, wherein the distance between the first electrode of said at least one pair of detection electrodes and the second electrode of said at least one pair of detection electrodes is comprised between 1 and 5 μm.

\* \* \* \* \*